(12) United States Patent
Kaufmann et al.

(10) Patent No.: US 8,530,172 B2
(45) Date of Patent: Sep. 10, 2013

(54) METHODS AND MATERIALS FOR ASSESSING ENZYME-NUCLEIC ACID COMPLEXES

(75) Inventors: Scott H. Kaufmann, Rochester, MN (US); Anand G. Patel, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 41 days.

(21) Appl. No.: 13/111,583

(22) Filed: May 19, 2011

(65) Prior Publication Data

US 2011/0287441 A1 Nov. 24, 2011

Related U.S. Application Data

(60) Provisional application No. 61/346,240, filed on May 19, 2010.

(51) Int. Cl.
*G01N 33/53* (2006.01)

(52) U.S. Cl.
USPC .............................................. 435/7.1; 435/7.2

(58) Field of Classification Search
None
See application file for complete search history.

(56) References Cited

U.S. PATENT DOCUMENTS

| | | | |
|---|---|---|---|
| 4,036,945 A | 7/1977 | Haber | |
| 4,331,647 A | 5/1982 | Goldenberg | |
| 2011/0287441 A1 | 11/2011 | Kaufmann | |
| 2011/0318380 A1* | 12/2011 | Brix et al. | 424/193.1 |

OTHER PUBLICATIONS

Campbell (Monoclonal Antibody Technology 1984 Elsevier Science Publisher).*
Gilboa et al. J. Biol. Chem. 2002 vol. 277, p. 19811-19816.*
Bertschinger et al. Protein Engineering & Design & Selection 2004 vol. 17, p. 699-707.*
Shuman et al. Molecular Microbiology 1995 vol. 17, p. 405-410.*
Andrew and Titus, "Fragmentation of Immunoglobulin G," *Current Protocols in Immunology*, 1997, Supplement 21, Unit 2.8, pp. 2.8.1-2.8.10.
Andrew and Titus, "Fragmentation of Immunoglobulin M," *Current Protocols in Immunology*, 2000, Supplement 38, Unit 2.10A, pp. 2.10A.1-2.10A.4.
Current Protocols in Immunology, section 2.6.7, 1991, 8 pages.
Baines et al., "Purification of Immunoglobulin G (IgG)," *Methods in Molecular Biology*, 1992, Chapter 8, 79-104.
Bjornsti et al., "Expression of human DNA topoisomerase I in yeast cells lacking yeast DNA topoisomerase I: restoration of sensitivity of the cells to the antitumor drug camptothecin," *Cancer Res*, Nov. 1989, 49:6318-6323.
Brown et al., "Antigen retrieval in cryostat tissue sections and cultured cells by treatment with sodium dodecyl sulfate (SDS)," *Histochem Cell Biol*, 1996, 105:261-267.
Buckwalter et al., "RNA synthesis inhibitors alter the subnuclear distribution of DNA topoisomerase I," *Cancer Res*, Apr. 1996, 56:1674-1681.
Champoux, "DNA Topoisomerases: Structure, Function, and Mechanism," *Ann Rev of Biochem*, 2001, 70:369-413.
Cheng and Shuman, "Recombinogenic Flap Ligation Pathway for Intrinsic Repair of Topoisomerase IB-Induced Double-Strand Breaks," *Mol Cell Biol*, Nov. 2000, 20:8059-8068.
Coligan et al., Unit 9, Current Protocols in Immunology, Wiley Interscience, 1994, 4 pages.
Cooper and Patterson, "Production of Polyclonal Antisera," in Current Protocols in Immunology, section 2.4.1, 2008, 10 pages.
Drygin, "Natural covalent complexes of nucleic acids and proteins: some comments on practice and theory on the path from well-known complexes to new ones," *Nucl Acids Res.*, 1998, 26(21):4791-4796.
Edelman et al., *Methods in Enzymology*, Academic Press, 1967, vol. 1, p. 422.
Eng et al., "Development of a stable camptothecin resistant subline of P388 leukemia with reduced topoisomerase I content," *Mol Pharmacol*, 1990, 38:471-480.
Eng et al., "Evidence that DNA topoisomerase I is necessary for the cytotoxic effects of camptothecin," *Mol Pharmacol*, 1988, 34:755-760.
Fiorani et al., "Domain interactions affecting human DNA topoisomerase I catalysis and camptothecin sensitivity," *Mol Pharmacol*, 1999, 56:1105-1115.
Gálvez-Peralta et al., "On the role of topoisomerase I in mediating the cytotoxicity of 9-aminoacridine-based anticancer agents," *Bioorg & Med Chem Lett*, 2009, 19:4459-4462.
Garg et al., "Role of DNA topoisomerase I in the transcription of supercoiled rRNA gene," *Proc Natl Acad Sci U S A*, May 1987, 84:3185-3188.
Green and Manson, "Production of Polyclonal Antisera" *Immunochemical Protocols* (Manson, ed.), Chapter 1, pp. 1-5 (Humana Press 1992).
Harlow et al., Antibodies: A Laboratory Manual,Cold Spring Harbor Pub. 1988 (Table of contents and p. 726 of index), 10 pages.
Hsiang et al., "DNA Topoisomerase I-mediated DNA Cleavage and Cytotoxicity of Camptothecin Analogues," *Cancer Res*, Aug. 1989, 49:4385-4389.
Ivanova et al., "Polyclonal antibodies against a structure mimicking the covalent linkage unit between picornavirus RNA and VPg: an immunochemical study," *Biochem*, 2005, 70(9):1038-1045.
Kaufmann and Svingen, "Immunoblot analysis and band depletion assays," *Methods Mol Biol*, 1999, 94:253-268.
Kaufmann et al., "Altered formation of topotecan-stabilized topoisomerase I-DNA adducts in human leukemia cells," *Blood*, Mar. 1997, 89(6):2098-2104.

(Continued)

*Primary Examiner* — Jacob Cheu
(74) *Attorney, Agent, or Firm* — Fish & Richardson P.C.

(57) ABSTRACT

This document relates to methods and materials involved in assessing samples for enzyme-nucleic acid complexes. For example, methods and materials for using antibodies to determine the presence, absence, or amount of enzyme-nucleic acid complexes (e.g., human topoisomerase I-DNA complexes) in a sample (e.g., a biological sample such as a tissue biopsy) are provided.

12 Claims, 5 Drawing Sheets

(56) References Cited

OTHER PUBLICATIONS

Kaufmann, "Reutilization of immunoblots after chemiluminescent detection," *Anal Biochem*, 2001, 296 283-286.

Kohler & Milstein, "Continuous cultures of fused cells secreting antibody of predefined specificity," *Nature*, Aug. 1975, 256:495-497.

Kohn, "DNA filter elution: A window on DNA damage in mammalian cells," *BioEssays*, 1996, 18:505-513.

Li and Liu, "Tumor cell death induced by topoisomerase-targeting drugs," *Ann Rev of Pharmacol and Toxicol*, 2001, 41:53-77.

Li et al., "beta-Lapachone, a novel DNA topoisomerase I inhibitor with a mode of action different from camptothecin," *J Biol Chem*, Oct. 1993, 268:22463-22468.

Liebes et al., "Pharmacodynamics of Topoisomerase I Inhibition: Western Blot Determination of Topoisomerase I and Cleavable Complex in Patients with Upper Gastrointestinal Malignancies Treated with Topotecan," *Clin. Can Res.*, Mar. 1998, 4:545-557.

Liu et al., "Cleavage of DNA by mammalian DNA topoisomerase II," *J Biol Chem*, Dec. 1983, 258:15365-15370.

Mattern et al., "Relationship between the Intracellular Effects of Camptothecin and the Inhibition of DNA Topoisomerase I in Cultured L1210 Cells," *Cancer Res*, Apr. 1987, 47:1793-1798.

Merino et al., "DNA topoisomerase I is involved in both repression and activation of transcription," *Nature, 1993*, 365:227-232.

Mow and Kaufmann, "Use of camptothecins in the treatment of leukemia and related disorders," in Adams VR, Burke TG (eds): *Camptothecins in Cancer Therapy*. Totowa, N.J., Humana Press, Inc., 2005, pp. 421-450.

Muller et al., "Association of type I DNA topoisomerase with herpes simplex virus," *J Gen Virol*, 1985, 66 ( Pt 7):1565-1574.

Muslimovic et al., "An optimized method for measurement of gamma-H2AX in blood mononuclear and cultured cells," *Nat Protoc*, 2008, 3:1187-1193.

Nisonhoff et al., "Separation of Univalent Fragments from the Bivalent Rabbit Antibody Molecule by Reduction of Disulfide Bonds," *Arch. Biochem. Biophys.*, 1960, 89:230-244.

Nitiss and Wang, "DNA topoisomerase-targeting antitumor drugs can be studied in yeast," *Proc Natl Acad Sci U S A*, Oct. 1988, 85:7501-7505.

Pommier and Cushman, "The indenoisoquinoline noncamptothecin topoisomerase I inhibitors: update and perspectives," *Mol. Canc. Ther.*, May 2009, 8:1008-1014.

Pommier, "Topoisomerase I inhibitors: camptothecins and beyond," *Nat Rev Cancer*, 2006, 6:789-802.

Porter, "The hydrolysis of rabbit γ-globulin and antibodies with crystalline papain," *Biochem. J.*, 1959, 73:119.

Sakaguchi et al., "Epitope distribution of Randomly Established Monoclonal Antibodies against Human Type II DNA Topoisomerases," *J Biochem*, 2002, 132:409-416.

Saleem et al., "Mechanisms of Resistance to Camptothecins," *Annals of the New York Academy of Sciences*, 2000, 922:46-55

Segovis et al., "PI3K Links NKG2D Signaling to a CrkL Pathway Involved in Natural Killer Cell Adhesion, Polarity, and Granule Secretion," *J Immunol*, 2009, 182:6933-6942.

Smith et al., "Measurement of protein using bicinchoninic acid," *Anal Biochem*, 1985, 150:76-85.

Staker et al., "Structures of three classes of anticancer agents bound to the human topoisomerase I-DNA covalent complex," *J Med Chem*, 2005, 48:2336-2345.

Staker et al., "The mechanism of topoisomerase I poisoning by a camptothecin analog," *Proc Natl Acad Sci*, Nov. 2002, 99(24):15387-15392.

Subramanian et al., "Analysis of Topoisomerase I/DNA Complexes in Patients Administered Topotecan," *Can Res.*, May 1995, 55:2097-2103.

Subramanian et al., "ICE Bioassay; DNA Topoisomerase Protocols : vol. II," *Enzymology and Drugs*, 2001, pp. 137-147.

Tuduri et al., "Topoisomerase I suppresses genomic instability by preventing interference between replication and transcription," *Nat Cell Biol*, 2009, 11:1315-1324.

Wang and Rogler, "Topoisomerase I-mediated integration of hepadnavirus DNA in vitro," *J Virol*, May 1991, 65(2):2381-2392.

Wang, "Cellular roles of DNA topoisomerases: a molecular perspective," *Nat Rev Mol Cell Biol*, Jun. 2002, 3:430-440.

Wu and Liu, "DNA looping alters local DNA conformation during transcription," *J Mol Biol*, 1991, 219:615-622.

Yokoyama, "Production of monoclonal antibodies," *Current Protocols in Immunology*, 1995, Unit 2.5 pp. 2.5.1-2.5.17.

\* cited by examiner

...-Leu-Gly-Thr-Ser-Lys-Leu-Asn-Tyr-Leu-Asp-Pro-Arg-Ile-Thr-Val-...

(SEQ ID NO:10)

```
      H. sapiens  LGTSKLNYLDPRITV (SEQ ID NO:11)
     M. musculus  LGTSKLNYLDPRITV (SEQ ID NO:12)
       G. gallus  LSTSKLNYLDPRISV (SEQ ID NO:13)
D. melanogaster   LGTSKLNYLDPRISV (SEQ ID NO:14)
      C. elegans  LGTSKLNYIDPRITV (SEQ ID NO:15)
   S. cerevisiae  LGTSKINYIDPRLSV (SEQ ID NO:16
```

METHODS AND MATERIALS FOR ASSESSING ENZYME-NUCLEIC ACID COMPLEXES

CROSS-REFERENCE TO RELATED APPLICATIONS

This application claims the benefit of U.S. Provisional Application Ser. No. 61/346,240, filed May 19, 2010. The disclosure of the prior application is considered part of (and is incorporated by reference in) the disclosure of this application.

BACKGROUND

1. Technical Field

This document relates to methods and materials involved in assessing samples for enzyme-nucleic acid complexes. For example, this document relates to methods and materials for using antibodies to determine the presence, absence, or amount of enzyme-nucleic acid complexes (e.g., human topoisomerase I-DNA complexes) in a sample (e.g., a biological sample such as a tissue biopsy).

2. Background Information

Topoisomerase I (topo I) is an abundant (up to 1,000,000 copies/cell) enzyme that relaxes torsional strain in DNA during the course of a variety of nuclear processes (Pommier, *Nat. Rev. Cancer*, 6:789-802 (2006); Wang, *Nat. Rev. Mol. Cell. Biol.*, 3:430-440 (2002); and Champoux, *Annual Review of Biochemistry*, 70:369-413 (2001)). Studies have demonstrated roles for topo I in replication, transcription, and viral integration. Additional studies have demonstrated that topo I is the target for a class of widely utilized anticancer drugs, the camptothecins (Eng et al., *Mol. Pharmacol.*, 34:755-760 (1988); and Bjornsti et al., *Cancer Res.*, 49:6318-6323 (1989)). In particular, irinotecan is approved for the treatment of colorectal cancer alone and in combination with 5-fluorouracil. This agent also has activity in non-small cell lung cancer, pancreatic cancer, and breast cancer. Topotecan (TPT), another camptothecin analogue, is approved for the treatment of ovarian and small cell lung cancer. In addition, this agent is currently being investigated for its potential activity in acute myelogenous leukemia. Additional novel topo I poisons continue to be developed and investigated (Pommier, *Nat. Rev. Cancer*, 6:789-802 (2006); Pommier and Cushman, *Mol. Canc. Ther.*, 8:1008-1014 (2009); and Mow and Kaufmann, Use of camptothecins in the treatment of leukemia and related disorders; In Adams V R, Burke T G (eds): Camptothecins in Cancer Therapy. Totowa, N.J., Humana Press, Inc., 2005, pp 421-450).

SUMMARY

This document relates to methods and materials involved in assessing samples for enzyme-nucleic acid complexes. For example, this document relates to methods and materials for using antibodies to determine the presence, absence, or amount of enzyme-nucleic acid complexes (e.g., human topoisomerase I-DNA complexes) in a sample (e.g., a biological sample such as a tissue biopsy).

A number of enzymes form covalent bonds with nucleic acid (e.g., DNA). Such enzymes included, without limitation, topo I, topoisomerase II (topo II), topoisomerase III (topo III), tyrosyl deoxynucleotidyl phosphodiesterase (TDP1), and yeast, protozoal, or bacterial topoisomerases (e.g., DNA gyrase, topoisomerase IV, and topoisomerase VI). A number of approved and investigational anti-cancer drugs target one or more of these enzymes. For example, camptothecin and its derivatives target topo I. These drugs induce cytotoxicity by preventing the religation step of topo I, resulting in an increase in the number of covalent topo I-DNA complexes. Subsequent collisions with replication forks and transcription complexes can produce DNA double-strand breaks that lead to cell death. The antibodies provided herein can be used to assess whether these covalent topo I-DNA complexes have been stabilized in tumor cells after drug administration. In the past, the measurement of these covalent topo I-DNA complexes within intact cells and tumors has been time consuming, laborious, and indirect. The antibodies provided herein (e.g., an α-TopoI cc monoclonal antibody) can specifically recognize the topo I-DNA covalent complex but not free topo I or free DNA. Such antibodies can be used for any appropriate immune-based assay (e.g., immunoblotting, immunofluorescence, or flow cytometry) to detect covalent topo I-DNA complexes in, for example, intact tumor cells and tissues.

Assessing the presence, absence, or amount of enzyme-nucleic acid complexes (e.g., human topoisomerase I-DNA complexes) in a sample (e.g., a biological sample such as a tissue biopsy) before and/or after a drug treatment designed to target an enzyme that forms a covalent bond with nucleic acid (e.g., an anti-cancer treatment) can allow clinicians and other medical professionals to monitor the effectiveness of that particular treatment.

In general, one aspect of this document features an isolated antibody preparation comprising, or consisting essentially of, an anti-enzyme-nucleic acid covalent complex antibody, wherein the anti-enzyme-nucleic acid covalent complex antibody binds to an enzyme-nucleic acid covalent complex and does not bind to the free form of the enzyme or the free form of the nucleic acid. The enzyme can be topoisomerase I. The enzyme can be topoisomerase II. The nucleic acid can be DNA. The nucleic acid can be human DNA. The anti-enzyme-nucleic acid covalent complex antibody can be produced using a polypeptide antigen having the amino acid sequence set forth in SEQ ID NO:1, 4, 5, or 8.

In another aspect, this document features a method for assessing a sample for enzyme-nucleic acid covalent complexes. The method comprises, or consists essentially of, performing an immune-based assay using an anti-enzyme-nucleic acid covalent complex antibody to detect the presence, absence, or amount of the enzyme-nucleic acid covalent complexes within the sample, wherein the anti-enzyme-nucleic acid covalent complex antibody binds to the enzyme-nucleic acid covalent complex and does not bind to the free form of the enzyme or the free form of the nucleic acid. The enzyme can be topoisomerase I. The enzyme can be topoisomerase II. The nucleic acid can be DNA. The nucleic acid can be human DNA. The anti-enzyme-nucleic acid covalent complex antibody can be produced using a polypeptide antigen having the amino acid sequence set forth in SEQ ID NO:1, 4, 5, or 8. The immune-based assay can comprise immunoblotting. The immune-based assay can comprise immunofluorescence. The immune-based assay can comprise flow cytometry. The sample can be a tissue biopsy sample. The sample can be a blood, bone marrow, or cancer tissue sample. The immune-based assay can comprise detecting the presence of the enzyme-nucleic acid covalent complex. The immune-based assay can comprise detecting the absence of the enzyme-nucleic acid covalent complex. The immune-based assay can comprise detecting the amount of the enzyme-nucleic acid covalent complex.

In another aspect, this document features a method for monitoring the effectiveness of a drug treatment designed to result in the accumulation of enzyme-nucleic acid covalent complexes within cells, wherein the method comprises performing an immune-based assay using an anti-enzyme-nucleic acid covalent complex antibody to detect the presence or absence of the accumulation of the enzyme-nucleic acid covalent complexes within a sample obtained from a mammal following treatment of the mammal with the drug treatment, wherein the anti-enzyme-nucleic acid covalent complex antibody binds to the enzyme-nucleic acid covalent complex and does not bind to the free form of the enzyme or the free form of the nucleic acid. The mammal can be a human. The drug treatment can be an irinotecan, topotecan, or camptothecin treatment. The method can comprise detecting the presence of the accumulation, thereby indicating that the drug treatment is effective. The method can comprise instructing the mammal to continue the drug treatment. The method can comprise detecting the absence of the accumulation, thereby indicating that the drug treatment is not effective. The method can comprise instructing the mammal to alter or discontinue the drug treatment. The enzyme can be topoisomerase I. The enzyme can be topoisomerase II. The nucleic acid can be DNA. The nucleic acid can be human DNA. The anti-enzyme-nucleic acid covalent complex antibody can be produced using a polypeptide antigen having the amino acid sequence set forth in SEQ ID NO:1, 4, 5, or 8. The immune-based assay can comprise immunoblotting. The immune-based assay can comprise immunofluorescence. The immune-based assay can comprise flow cytometry or immunohistochemistry. The sample can be a tissue biopsy sample. The sample can be a blood, bone marrow, or cancer tissue sample.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
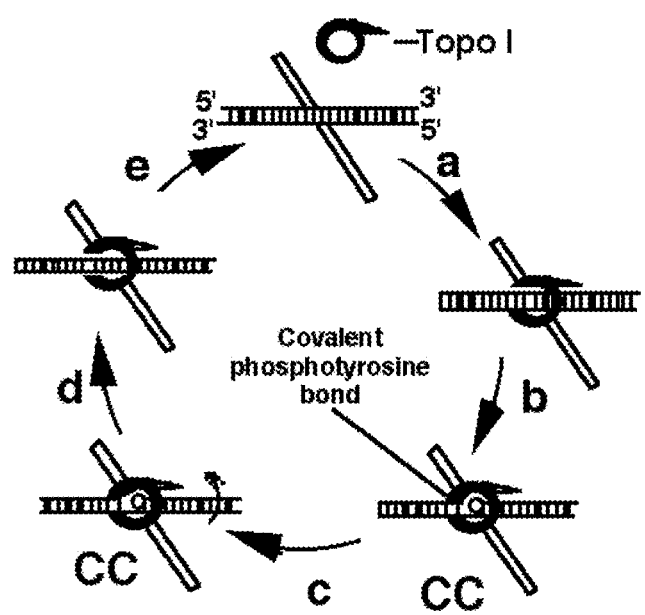
FIG. 1 is a diagram of the catalytic cycle of topo I. Initially, the enzyme binds to sites of supercoiled DNA ('a'). The enzyme creates a nick via a transesterification reaction catalyzed by an active site tyrosine residue ('b'), resulting in a topo I-DNA covalent complex ('cc'). DNA is allowed to rotate about the nick ('c'). After relaxation, the enzyme reverses the transesterification, resealing the nicked DNA ('d'), and disassociating from DNA ('e'). Camptothecin and its analogues inhibit the resealing of topo I-DNA covalent complexes ('d').

This document provides methods and materials involved in assessing samples for enzyme-nucleic acid complexes. For example, this document provides antibodies, antibody preparations, hybridomas, methods for making antibodies, methods for making hybridomas, methods for using antibodies to determine the presence, absence, or amount of enzyme-nucleic acid complexes (e.g., human topoisomerase I-DNA covalent complexes) in a sample (e.g., a biological sample such as a tissue biopsy), and methods for monitoring the effectiveness of a drug treatment designed to result in the accumulation of enzyme-nucleic acid complexes (e.g., human topoisomerase I-DNA covalent complexes) within cells.

As described herein, this document provides antibodies having the ability to bind to enzyme-nucleic acid covalent complexes (e.g., human topoisomerase I-DNA covalent complexes). The enzyme can be any appropriate enzyme including, without limitation, topo I (e.g., human topoI), topo II (e.g., human topo II), topo III, TDP1, and yeast, protozoal, or bacterial topoisomerases (e.g., DNA gyrase, topoisomerase IV, and topoisomerase VI). The nucleic acid can be any type of nucleic acid including, without limitation, genomic DNA (e.g., genomic human DNA), plasmid DNA, or DNA from pathogenic organisms such as yeast, bacteria, or protozoa. In some cases, the antibodies provided herein can bind to human topo I-DNA covalent complexes. Such antibodies can be generated using a polypeptide having the sequence set forth in SEQ ID NO:1 as an immunogen. In some cases, the antibodies provided herein can bind to human topo II-DNA covalent complexes. Such antibodies can be generated using a polypeptide having the sequence set forth in SEQ ID NO:4 or 5 as an immunogen. In some cases, the antibodies provided herein can bind to human TDP1-DNA covalent complexes. Such antibodies can be generated using a polypeptide having the sequence set forth in SEQ ID NO:8 as an immunogen. In some cases, an antibody provided herein can bind to an enzyme-nucleic acid covalent complex, but lack binding to the free form of the enzyme and/or lack binding to the free form of the nucleic acid. For example, an anti-topoisomerase I-DNA covalent complex antibody provided herein can bind to topoisomerase I-DNA covalent complexes and not bind to free topoisomerase I polypeptides or free DNA.

The term "antibody" as used herein refers to intact antibodies as well as antibody fragments that retain some ability to bind an epitope. Such fragments include, without limitation, Fab, F(ab')2, and Fv antibody fragments. The term "epitope" refers to an antigenic determinant on an antigen to which the paratope of an antibody binds. Epitopic determinants usually consist of chemically active surface groupings of molecules (e.g., amino acid residues amino acid-nucleic acid linkages) and usually have specific three dimensional structural characteristics as well as specific charge characteristics.

The antibodies provided herein can be any monoclonal or polyclonal antibody having specific binding affinity for an enzyme-nucleic acid covalent complex as opposed to the individual polypeptide subunit or the individual nucleic acid component. Such antibodies can be used in immunoassays in liquid phase or bound to a solid phase. For example, the antibodies provided herein can be used in competitive and non-competitive immunoassays in either a direct or indirect format. Examples of such immunoassays include the radioimmunoassay (RIA) and the sandwich (immunometric) assay.

Antibodies provided herein can be prepared using any method. For example, a polypeptide having the sequence set forth in SEQ ID NO:1, 4, 5, or 8 can be used as an immunogen to elicit an immune response in an animal such that specific antibodies are produced. In addition, the immunogen used to immunize an animal can be chemically synthesized or derived from translated cDNA. Further, the immunogen can be conjugated to a carrier polypeptide, if desired. Commonly used carriers that are chemically coupled to an immunizing polypeptide include, without limitation, keyhole limpet hemocyanin (KLH), thyroglobulin, bovine serum albumin (BSA), and tetanus toxoid.

The preparation of polyclonal antibodies is well-known to those skilled in the art. See, e.g., Green et al., Production of Polyclonal Antisera, in IMMUNOCHEMICAL PROTOCOLS (Manson, ed.), pages 1 5 (Humana Press 1992) and Coligan et al., Production of Polyclonal Antisera in Rabbits, Rats, Mice and Hamsters, in CURRENT PROTOCOLS IN IMMUNOLOGY, section 2.4.1 (1992). In addition, those of skill in the art will know of various techniques common in the immunology arts for purification and concentration of polyclonal antibodies, as well as monoclonal antibodies (Coligan et al., Unit 9, Current Protocols in Immunology, Wiley Interscience, 1994).

The preparation of monoclonal antibodies also is well-known to those skilled in the art. See, e.g., Kohler & Milstein, *Nature* 256:495 (1975); Coligan et al., sections 2.5.1 2.6.7; and Harlow et al., ANTIBODIES: A LABORATORY MANUAL, page 726 (Cold Spring Harbor Pub. 1988). Briefly, monoclonal antibodies can be obtained by injecting mice with a composition comprising an antigen, verifying the presence of antibody production by analyzing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well established techniques. Such isolation techniques include affinity chromatography with Protein A Sepharose, size exclusion chromatography, and ion exchange chromatography. See, e.g., Coligan et al., sections 2.7.1 2.7.12 and sections 2.9.1 2.9.3; Barnes et al., Purification of Immunoglobulin G (IgG), in METHODS IN MOLECULAR BIOLOGY, VOL. 10, pages 79 104 (Humana Press 1992).

In addition, methods of in vitro and in vivo multiplication of monoclonal antibodies are well known to those skilled in the art. Multiplication in vitro can be carried out in suitable culture media such as Dulbecco's Modified Eagle Medium or RPMI 1640 medium, optionally replenished by mammalian serum such as fetal calf serum, or trace elements and growth sustaining supplements such as normal mouse peritoneal exudate cells, spleen cells, and bone marrow macrophages. Production in vitro provides relatively pure antibody preparations and allows scale up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells (e.g., syngeneic mice) to cause growth of antibody producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Antibody fragments can be prepared by proteolytic hydrolysis of an intact antibody or by the expression of a nucleic acid encoding the fragment. Antibody fragments can be obtained by pepsin or papain digestion of intact antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. In some cases, an enzymatic cleavage using pepsin can be used to produce two monovalent Fab' fragments and an Fc fragment directly. These methods are described, for example, by Goldenberg (U.S. Pat. Nos. 4,036, 945 and 4,331,647). See, also, Nisonhoff et al., *Arch. Biochem. Biophys.*, 89:230 (1960); Porter, *Biochem. J.*, 73:119 (1959); Edelman et al., METHODS IN ENZYMOLOGY, VOL. 1, page 422 (Academic Press 1967); and Coligan et al. at sections 2.8.1 2.8.10 and 2.10.1 2.10.4.

Other methods of cleaving antibodies, such as separation of heavy chains to form monovalent light heavy chain fragments, further cleavage of fragments, or other enzymatic, chemical, or genetic techniques may also be used to provide fragments that retain some ability to bind (e.g., selectively bind) its epitope.

The antibodies provided herein can be substantially pure. The term "substantially pure" as used herein with reference to an antibody means the antibody is substantially free of other polypeptides, lipids, carbohydrates, and nucleic acid with which it is naturally associated in nature. Thus, a substantially pure antibody is any antibody that is removed from its natural environment and is at least 60 percent pure. A substantially pure antibody can be at least about 65, 70, 75, 80, 85, 90, 95, or 99 percent pure.

This document also provides methods for determining the presence, absence, or amount of enzyme-nucleic acid complexes (e.g., human topoisomerase I-DNA covalent complexes) within a sample (e.g., a biological sample such as a tissue biopsy). Such methods include using an antibody provided herein in an immune-based assay to detect the presence, absence, or amount of enzyme-nucleic acid complexes within a sample obtained from a mammal Any appropriate sample can be used. For example, tissue biopsies obtained from hematological malignancies (e.g., leukemia and lymphoma), solid tumors (e.g., non-small cell lung cancer, small cell lung cancer, colon cancer, and ovarian cancer), or tissue harboring infectious organisms containing topoisomerases can be obtained from a mammal and assessed for enzyme-nucleic acid complexes. In some cases, a sample of circulating tumor cells, cellular lysate, or partially purified enzyme sample can be assessed for enzyme-nucleic acid complexes. A sample to be assessed for enzyme-nucleic acid complexes can be obtained from any mammal including, without limitation, humans, non-human primates, dogs, rats, and mice. Any appropriate immune-based assays can be used to detect the presence, absence, or amount of enzyme-nucleic acid complexes within a sample. For example, immunoblotting, immunofluorescence, flow cytometry, ELISA, or immunohistochemistry can be used to detect covalent topo I-DNA complexes.

This document also provides methods for monitoring the effectiveness of a drug treatment designed to result in the accumulation of enzyme-nucleic acid complexes (e.g., human topoisomerase I-DNA covalent complexes) within cells. For example, a mammal (e.g., a human) with cancer treated with TPT, camptothecin, or irinotecan can be assessed using the antibodies provided herein to determine if cells within the mammal accumulate enzyme-nucleic acid complexes. The accumulation of enzyme-nucleic acid complexes following drug treatment can indicate that the treatment is effective. In such cases, the mammal can be instructed to continue the treatment. A lack of accumulated enzyme-nucleic acid complexes following drug treatment can indicate that the treatment is not effective. In such cases, the mammal can be instructed to adjust or discontinue the treatment.

In some cases, the methods and materials provided herein can be used to assist medical or research professionals in determining whether or not a particular drug treatment is effective. Medical professionals can be, for example, doctors, nurses, medical laboratory technologists, and pharmacists. Research professionals can be, for example, principle investigators, research technicians, postdoctoral trainees, and graduate students. A professional can be assisted by (1) determining whether or not a mammal (e.g., a human) accumulates enzyme-nucleic acid complexes (e.g., human topoisomerase I-DNA covalent complexes) within cells following treatment, and (2) communicating information about the presence or absence of such an accumulation to that professional.

Any appropriate method can be used to communicate information to another person (e.g., a professional). For example, information can be given directly or indirectly to a professional. In addition, any type of communication can be used to communicate the information. For example, mail, e-mail, telephone, and face-to-face interactions can be used. The information also can be communicated to a professional by making that information electronically available to the professional. For example, the information can be communicated to a professional by placing the information on a computer database such that the professional can access the information. In addition, the information can be communicated to a hospital, clinic, or research facility serving as an agent for the professional.

The invention will be further described in the following examples, which do not limit the scope of the invention described in the claims.

EXAMPLES

Example 1

Figure 2:
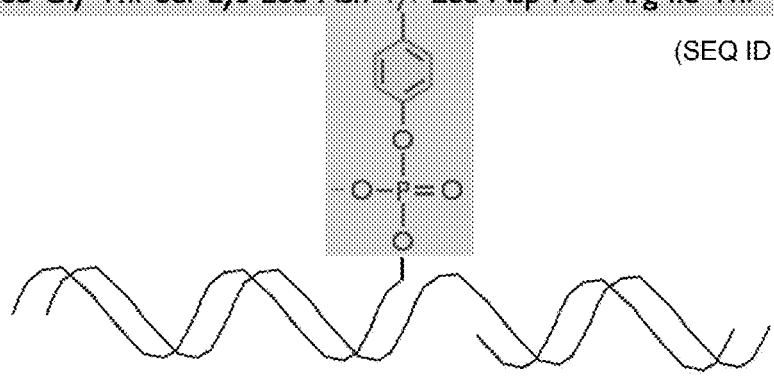
FIG. 2 is a diagram of the topo I-DNA covalent complex (top panel). A mouse monoclonal antibody with specificity for an epitope specific to topo I when it is bound to DNA (shown in shading) was raised. The sequence has high conservation among many organisms (bottom panel).

Generation and Characterization of Monoclonal Antibody Against Human Topoisomerase I-DNA Covalent Complexes The following was performed to develop a mouse monoclonal antibody (α-TopoI cc) that specifically binds to topo I-DNA complexes and not to free topo I polypeptides or free DNA. Topo I, when bound to DNA, forms a phosphodiester bond between a catalytic tyrosine residue and the 3'-end of DNA (FIG. 2). It was hypothesized that an antibody directed against an epitope containing the topo I active site tyrosine covalently bound to phosphate would recognize topo I when it is covalently bonded to DNA via a phosphodiester linkage. Consistent with this hypothesis, the resulting antibody was capable of detecting topo I-DNA covalent complexes by immunoblotting, immunofluorescence, or flow cytometry.

Polypeptides

Polypeptides generated using standard f-moc protein chemistry included: phospho-topo I active site (CLGTSKLN(phosphoY)LDPRITV; SEQ ID NO:1), topo I active site (CLGTSKLNYLDPRITV; SEQ ID NO:2), and phosphotyrosine polypeptide ($CX_7$(phospho-Y)$X_7$, where X is a random mixture of amino acids; SEQ ID NO:3). The N-terminal "C" is a cysteine residue that can be used to conjugate the polypeptide to various proteins for ELISA or inoculation.

Immunization

Female BALB/c mice were immunized by subcutaneous injection of 1-2 mg phospho-topo I active site peptide in complete Freund's adjuvant (Sigma; St. Louis, Mo.) followed by with antigen in incomplete Freund's adjuvant. After bleeds were tested for immunoreactivity by enzyme-linked immunosorbent assay (ELISA), $10^8$ splenocytes from the mouse with the strongest reactivity were fused with F/O myeloma cells (non-secreting myeloma derived from SP2/0 Balb/c myeloma cells) using PEG1500 (Roche Molecular Biochemicals; Mannheim, Germany), then grown in hypoxanthine-aminopterin-thymidine (HAT) selection medium containing 5 U/mL of recombinant mouse interleukin-6 (IL-6) (Roche Molecular Biochemicals). At day 10 after fusion, hybridoma culture supernatants were screened by ELISA and ICE assay. Cells in positive wells were subcloned twice by limiting dilution.

ELISA

Ninety-six well dishes were coated with 25 ng peptide/well (phospho-topo I active site, topo I active site, or phosphotyrosine peptide) in 100 mM sodium carbonate buffer, washed, and blocked with 5% milk in PBS. To test each well, 50 μL hybridoma culture supernatant was applied for 1 hour at 20-22° C. Plates were washed with sodium carbonate buffer, incubated with alkaline phosphatase-conjugated goat anti-mouse IgG (Sigma) for 1 hour, washed, reacted with 100 μL of 1 mg/mL p-nitrophenyl phosphate, and assayed for absorbance at 405 nm. Positive clones were confirmed by ICE assay.

Cell Culture

F/O myeloma cells were grown in IMDM supplemented with 10% (v/v) FCS, 100 U penicillin, 100 µg/mL streptomycin, and 2 mM L-glutamine. A549 and K562 cells were grown in RPMI 1640 medium supplemented with 10% (v/v) FCS, 100 U penicillin, 100 µg/mL streptomycin, and 2 mM L-glutamine (medium A). P388/WT and P388/CPT cells were grown in medium A supplemented with 100 µM 2-mercaptoethanol. The CPT cells were grown in medium A supplemented with 10 µM camptothecin. All cells were propagated at 37° C. in a humidified incubator with 5% $CO_2$.

In Vivo Complexing of Enzyme (ICE) Assays

ICE assays were performed as described elsewhere (Subramanian et al., ICE Bioassay; DNA Topoisomerase Protocols: Volume II: Enzymology and Drugs, 2001, pp 137-147; and Gálvez-Peralta et al., *Bioorganic & Medicinal Chemistry Letters*, 19:4459-4462 (2009)). Briefly, A549 cells grown to 40-60% confluence in 100 mm tissue culture dishes were treated for 60 minutes with 0.1% (v/v) DMSO, 10 µM TPT, or 10 µM etoposide in serum-free RPMI containing 10 mM HEPES, pH 7.4 (medium B). At the end of the incubation, the medium was aspirated, and the cells were rapidly lysed in 1 mL lysis buffer consisting of 1% (w/v) sarkosyl, 10 mM Tris-HCl (pH 8.0 at 20-22° C.) and 1 mM EDTA. Lysate was layered on a cesium chloride gradient and ultracentrifuged at 125,000 g for 21 hours at 20° C. After centrifuge tubes were perforated at the bottom with a 23-gauge needle, 0.5 mL fractions were collected, assayed for the presence of DNA (detectable in fractions 1-4), and slot-blotted onto nitrocellulose membranes. Membranes were then blocked in 5% (w/v) milk in 150 nM NaCl containing 10 mM Tris-HCl (pH 7.4 at 20-22° C.) for 2 hours and incubated in either C-21 anti-topo I IgM antibody (obtained from Y.-C. Cheng; Yale University; New Haven, Conn.) or the α-TopoI cc antibody (diluted to 1 µg/mL in blocking buffer). Western blotting was performed as described elsewhere (Kaufmann, *Anal. Biochem.*, 296:283-286 (2001)).

Band Depletion Assays

Band depletion assays were performed as described elsewhere (Kaufmann and Svingen, *Methods Mol. Biol.*, 94:253-268 (1999)). A549 cells grown in 100 mm culture dishes to 40-60% confluence were treated with increasing concentrations of TPT in medium B for 60 minutes. After treatment, cells were immediately solubilized in 6 M guanidine hydrochloride containing 250 mM Tris-HCl (pH 8.5 at 20° C.), 10 mM EDTA, 1% (v/v) 2-mercaptoethanol, and 1 mM freshly added phenylmethylsulfonyl fluoride. After preparation, for electrophoresis as described elsewhere (Kaufmann et al., *Blood*, 89:2098-2104 (1997), aliquots containing 50 mg of protein (determined by the bicinchoninic acid method (Smith et al., *Anal. Biochem.*, 150:76-85 (1985)) were either slot blotted for immunoblotting with α-TopoI cc antibody or separated on SDS-polyacrylamide gels, eletrophoretically transferred to nitrocellulose, and probed with C-21 anti-Topo I or, as a loading control anti-Hsp90 mouse (obtained from D. O. Toft; Mayo Clinic; Rochester, Minn.).

Immunofluorescence

Immunofluorescence studies in A549 cells were performed as described elsewhere (Segovis et al., *J. Immunol.*, 182:6933-6942 (2009)) with several modifications. After cells grown on nitric acid-etched coverslips were treated for 1 hour with TPT in medium B, coverslips were fixed in 2% (w/v) paraformaldehyde in calcium- and magnesium-free Dulbecco's phosphate buffered saline (PBS) for 10 minutes at room temperature, washed with PBS, and permeabilized with 0.25% (v/v) Triton X-100 in PBS for 5 minutes. To denature DNA-protein crosslinks, the coverslips were incubated in 1% SDS for 5 minutes (Brown et al., *Histochem. Cell Biol.*, 105:261-267 (1996)), washed three times with PBS, and incubated in a blocking buffer consisting of PBS, 1% (v/v) glycerol, 0.1% glycerol from cold water fish, 5% (v/v) normal goat serum, 0.1% (w/v) BSA, and 0.4% (w/v) sodium azide. Coverslips were incubated overnight in primary antibody, followed by staining with Alexa Fluor 488-, 568-, or 647-conjugated secondary antibody (Invitrogen) diluted at a ratio of 1:1000. α-TopoI cc antibody was used at 1.2 µg/mL, and α-Topo I human IgG (Topogen; Port Orange, Fla.) was used at 1:1000. Coverslips were counterstained with 1 mg/mL Hoechst 33258 in PBS and mounted using ProLong antifade reagent (Invitrogen; Carlsbad, Calif.). Images were captured on a LSM 710 scanning confocal microscope (Carl Zeiss AG; Oberkochen, Germany) using a 63×/1.2 W Korr C-Apo objective. Quantitation and image processing were performed using the Zeiss Zen software package and Adobe Photoshop CS3.

Flow Cytometry

A549 and K562 cells were stained using a modified protocol of a protocol described elsewhere (Muslimovic et al., *Nat. Protoc.*, 3:1187-1193 (2008)). After $10^6$ cells were treated for 1 hour with TPT in medium B, samples were centrifuged at 300 g for 5 minutes. Cells were then partially lysed for 1 minute in 100 µL extraction buffer, which consisted of 25 mM Tris-HCl (pH 7.5 at 20-22° C.), 1% (w/v) Triton X-100, 1 mM EDTA, 0.01% (w/v) BSA, and 0.2% (w/v) paraformaldehyde then fixed for 10 minutes at 20-22° C. by addition of 1 mL 2% (w/v) paraformaldehyde in PBS. Nuclei were pelleted and incubated for 60 minutes in 100 µL blocking buffer with primary antibody (1 µg/mL for A549 and P388 cells; and 5 µg/mL for K562 cells). Nuclei were washed by addition of 2 mL PBS, pelleted, and incubated for 30 minutes in 100 µL blocking buffer with 1 µg/mL Alexa Fluor 647-conjugated goat anti-mouse IgG (Invitrogen). Nuclei were washed by addition of 2 mL PBS, pelleted, and immediately analyzed on a FACSCanto II flow cytometer (BD Biosciences; San Jose, Calif.) on the APC channel (excitation: 633 nm; emission: 660/20 nm).

Results

It was hypothesized that a phospho-specific antibody directed to the active site tyrosine (Y723) of topo I would detect topo I covalently attached to DNA. After a 15-mer polypeptide centered on phosphorylated Y723 (FIG. 2) was injected into mice, hybridomas were produced and screened for the ability to detect covalent topo I-DNA covalent complexes. A subclone that exhibited high specificity for phospho-topo I polypeptide, as well as specificity for TPT-stabilized topo I-DNA complexes, was isolated for further analysis. The antibody, termed "α-TopoI cc," was purified from hybridoma supernatants and used for the following studies. The hybridoma was assigned a Topo Icc designation.

Detection Via Immunoblotting

α-TopoI cc detected topo I-DNA complexes with high specificity. ICE assays were used to separate DNA-bound and free protein following treatment with topoisomerase poisons. The α-TopoI cc antibody detected topo I that co-migrates with DNA following exposure to 10 µM topotecan (FIG. 3A) but failed to detect any other protein fraction (the DNA fractions of untreated or etoposide treated cells, or free topo I), demonstrating specificity for covalent topo I-DNA complexes.

Figure 3:
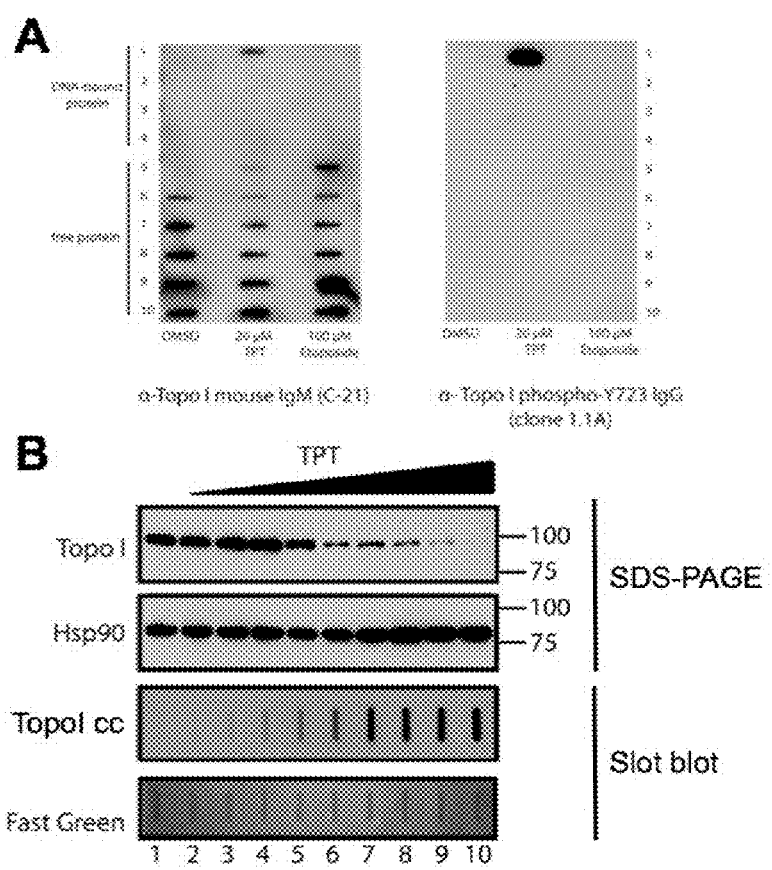
FIG. 3 contains photographs of immunoblots showing the detection of topo I-DNA covalent complexes. A, in vivo complexing of enzyme (ICE) assays were used to separate topo I-DNA covalent complexes from free topo I in A549 cell lysates. Fractions were immobilized onto a nitrocellulose membrane and blotted with either a topo I antibody (left) or the α-TopoI cc antibody (right). B, a band depletion assay was performed by treating A549 cell with diluent (lane 1) or 2× serial dilutions up to 100 μM TPT (lanes 2-10). Aliquots containing equal amounts of protein were either subjected to SDS-PAGE and probed with antibodies to topo I and Hsp90 (top two panels) or slot-blotted onto membranes and probed for topo I-DNA covalent complexes with α-TopoI cc antibody (bottom two panels).

To further characterize the antibody, band depletion assays were performed. These assays were used in the past (Kaufmann and Svingen, *Methods Mol. Biol.*, 94:253-268 (1999)) to demonstrate covalent attachment of topo I to DNA. When cells are treated with increasing TPT concentrations, standard SDS-PAGE followed by immunoblotting for total topo I demonstrates a graduated decrease in the topo I signal at 100 kDa, as enzyme covalently attached to DNA does not migrate in the polyacrylamide gels (FIG. 3B, top panel). When lysates from these cells were slot-blotted onto membranes and probed with α-TopoI cc, a corresponding increase in signal for topo I-DNA covalent complexes was detected as TPT concentration increases (FIG. 3B, bottom panel).

Optical Morphology and Flow Cytometry

Figure 4:
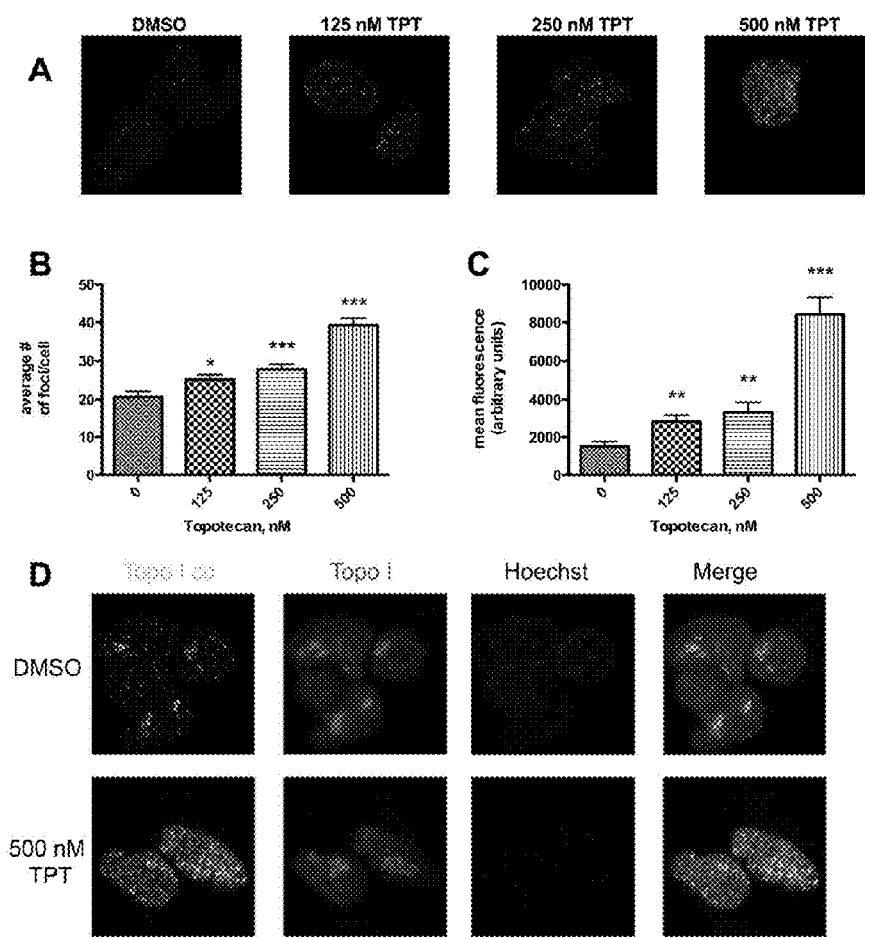
FIG. 4 contains photographs showing the detection of topo I-DNA covalent complexes in intact cultured cells via microscopy. Panel A includes photographs of A549 cells that were grown on coverslips, stained with α-TopoI cc antibody (which stained green), and counterstained for DNA using Hoechst 33258 (which stained blue). Panel B is a graph plotting foci numbers for at least 30 cells treated with each TPT concentration. Panel C is a graph plotting maximal mean fluorescence for 25 cells. Error bars represent s.e.m., and graphs are representative of three experiments. Panel D contains photographs of double staining of topo I-DNA covalent complexes (which stained green) and total topo I (which stained red) in A549 cells.

In addition to detecting topo I-DNA covalent complexes in cell lysates, α-TopoI cc was able to detect topo I-DNA complexes within intact cells and tissues. To this end, assays were developed to detect topo I-DNA complexes using indirect fluorescent microscopy and flow cytometry. Due to the inaccessibility of the epitope, a 1% sodium dodecylsulfate wash was used to improve staining intensity (Brown et al., *Histochem. Cell Biol.*, 105:261-267 (1996)). After treatment of A549 cells with TPT, an increase in staining intensity was detected by confocal microscopy (FIG. 4A). This staining intensity exhibited a dose-dependent increase when quantitated as average number of foci per cell (FIG. 4B) or maximal mean fluorescence at a confocal slice (FIG. 4C). Double staining with a topo I antibody and α-TopoI cc revealed that marginal staining with α-TopoI cc was detectable in the nucleoli of untreated cells and that TPT caused a dramatic increase in non-nucleolar staining of topo I-DNA complexes (FIG. 4D). This correlates with previously observed migration of topo I out of nucleoli following TPT treatment (Buckwalter et al., *Cancer Res.*, 56:1674-1681 (1996)).

Figure 5:
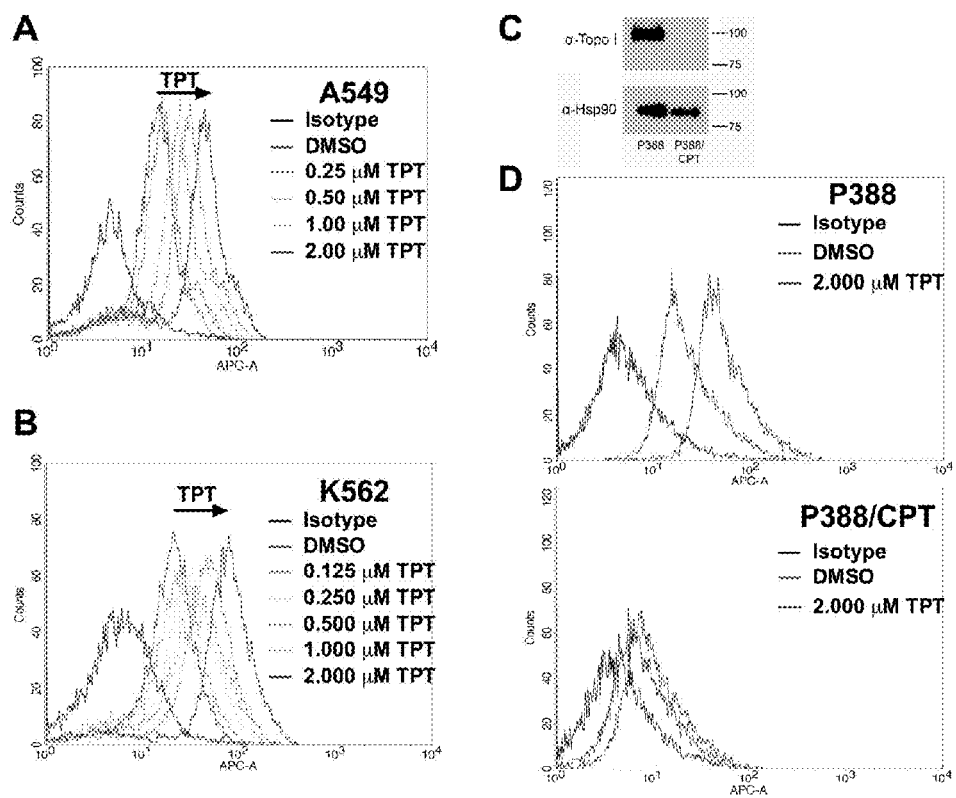
FIG. 5 contains results demonstrating the detection of topo I-DNA covalent complexes via flow cytometry. Panel A is a graph plotting the detection of topo I-DNA covalent complexes in A549 cells using flow cytometry. Panel B is a graph plotting the detection of topo I-DNA covalent complexes in K562 cells using flow cytometry. Panel C contains photographs of gels of cell lysates of P388 and P388/CPT mouse lymphoma lines that were probed for topo I and, as a loading control, heat shock protein 90 (Hsp90). Panel D contains graphs plotting the detection of topo I-DNA covalent complexes in P388 and P388/CPT cells by flow cytometry.

Flow cytometry is a highly automated method for rapidly quantitating the fluorescence of thousands of individual cells or nuclei per treatment. Using this method, topo I-DNA covalent complexes were detectable as rightward shifts in staining intensity. Topo I-DNA covalent complexes were detected in both A549 (FIG. 5A) and K562 (FIG. 5B) cells. To test for the specificity of the α-TopoI cc, staining for topo I-DNA complexes in a camptothecin-resistant mouse lymphoma line, P388/CPT cells (Eng et al., *Mol. Pharmacol.*, 38:471-480 (1990)) which lack detectable topo I protein, was performed (FIG. 5C). In wild-type P388 cells, a rightward shift was detectable following treatment with 2 µM TPT (FIG. 5D, top panel). In contrast, this shift was not observed in P388/CPT cells (FIG. 5D, bottom panel), again demonstrating specificity of α-TopoI cc antibody for covalent topo I-DNA complexes in intact cells.

Example 2

Generation and Characterization of Monoclonal Antibodies Against Human Topoisomerase II-DNA Covalent Complexes The following is performed to develop a mouse monoclonal antibody (α-TopoII cc) that specifically binds to topo II-DNA complexes and not to free topo II polypeptides or free DNA. Topo II, when bound to DNA, forms a phosphodiester bond between a catalytic tyrosine residue and the 5'-end of DNA. It is hypothesized that an antibody directed against an epitope containing the topo II active site tyrosine covalently bound to phosphate would recognize topo II when it is covalently bonded to DNA via a phosphodiester linkage. Resulting antibodies are capable of detecting topo II-DNA covalent complexes by immunoblotting, immunofluorescence, or flow cytometry.

Polypeptides

The following polypeptides are generated using standard f-moc protein chemistry: phospho-topo IIα active site (CKD-SASPR(phosphoY)IFTMLSS; SEQ ID NO:4), phospho-topo IIβ active site (CKDAASPR(phosphoY)IFTMLST; SEQ ID NO:5), topo IIα active site (CKDSASPRYIFTMLSS; SEQ ID NO:6), topo IIβ active site (CKDAASPRYIFTMLST; SEQ ID NO: 7) and phosphotyrosine polypeptide ($CX_7$(phospho-Y)$X_7$, where X is a random mixture of amino acids; SEQ ID NO:3).

Immunization

Female BALB/c mice are immunized by subcutaneous injection of 1-2 mg phospho-topo IIα or β active site peptide in complete Freund's adjuvant (Sigma; St. Louis, Mo.) followed by with antigen in incomplete Freund's adjuvant. After bleeds are tested for immunoreactivity by enzyme-linked immunosorbent assay (ELISA), $10^8$ splenocytes from the mouse with the strongest reactivity are fused with F/O myeloma cells (non-secreting myeloma derived from SP2/0 Balb/c myeloma cells) using PEG1500 (Roche Molecular Biochemicals; Mannheim, Germany), then are grown in hypoxanthine-aminopterin-thymidine (HAT) selection medium containing 5 U/mL of recombinant mouse interleukin-6 (IL-6) (Roche Molecular Biochemicals). At day 10 after fusion, hybridoma culture supernatants are screened by ELISA and ICE assay. Cells in positive wells are subcloned twice by limiting dilution.

ELISA

Ninety-six well dishes are coated with 25 ng peptide/well (phospho-topo IIα or β active site, topo II active site, or phosphotyrosine peptide) in 100 mM sodium carbonate buffer, are washed, and are blocked with 5% milk in PBS. To test each well, 50 µL hybridoma culture supernatant is applied for 1 hour at 20-22° C. Plates are washed with sodium carbonate buffer, are incubated with alkaline phosphatase-conjugated goat anti-mouse IgG (Sigma) for 1 hour, are washed, are reacted with 100 µL of 1 mg/mL p-nitrophenyl phosphate, and are assayed for absorbance at 405 nm. Positive clones are confirmed by ICE assay.

Example 3

Generation and Characterization of Monoclonal Antibodies Against Human TDP1-DNA Covalent Complexes The following is performed to develop a mouse monoclonal antibody (α-TDP1cc) that specifically binds to TDP1-DNA complexes and not to free TDP1 polypeptides or free DNA. Resulting antibodies are capable of detecting TDP1-DNA covalent complexes by immunoblotting, immunofluorescence, or flow cytometry.

Polypeptides

The following polypeptides are generated using standard f-moc protein chemistry: phospho-TDP1 active site (C-DI-AFGTH(phosphoH)TKMMLLL; SEQ ID NO:8), TDP1 active site (CDIAFGTHHTKMMLLL; SEQ ID NO:9), and phosphotyrosine polypeptide ($CX_7$(phospho-Y)$X_7$, where X is a random mixture of amino acids; SEQ ID NO:3).

Immunization

Female BALB/c mice are immunized by subcutaneous injection of 1-2 mg phospho-TDP1 active site peptide in complete Freund's adjuvant (Sigma; St. Louis, Mo.) followed by with antigen in incomplete Freund's adjuvant. After bleeds are tested for immunoreactivity by enzyme-linked immunosorbent assay (ELISA), $10^8$ splenocytes from the mouse with the strongest reactivity are fused with F/O myeloma cells (non-secreting myeloma derived from SP2/0 Balb/c myeloma cells) using PEG1500 (Roche Molecular Biochemicals; Mannheim, Germany), then are grown in hypoxanthine-aminopterin-thymidine (HAT) selection medium containing 5 U/mL of recombinant mouse interleukin-6 (IL-6) (Roche Molecular Biochemicals). At day 10 after fusion, hybridoma culture supernatants are screened by ELISA and ICE assay. Cells in positive wells are subcloned twice by limiting dilution.

ELISA

Ninety-six well dishes are coated with 25 ng peptide/well (phospho-TDP1 active site, TDP1 active site, or phosphotyrosine peptide) in 100 mM sodium carbonate buffer, are washed, and are blocked with 5% milk in PBS. To test each well, 50 µL hybridoma culture supernatant is applied for 1 hour at 20-22° C. Plates are washed with sodium carbonate buffer, are incubated with alkaline phosphatase-conjugated goat anti-mouse IgG (Sigma) for 1 hour, are washed, are reacted with 100 µL of 1 mg/mL p-nitrophenyl phosphate, and are assayed for absorbance at 405 nm. Positive clones are confirmed by ICE assay.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated antibody preparation comprising an anti-enzyme-nucleic acid covalent complex antibody, wherein said anti-enzyme-nucleic acid covalent complex antibody binds to an enzyme-nucleic acid covalent complex and does not bind to the free form of said enzyme or the free form of said nucleic acid, wherein said enzyme is selected from the group consisting of topoisomerase I, topoisomerase II, topoisomerase III, tyrosyl deoxynucleotidyl phosphodiesterase, yeast topoisomerases, protozoal topoisomerases, and bacterial topoisomerases.

2. The isolated antibody preparation of claim 1, wherein said enzyme is topoisomerase I.

3. The isolated antibody preparation of claim 1, wherein said enzyme is topoisomerase II.

4. The isolated antibody preparation of claim 1, wherein said nucleic acid is DNA.

5. The isolated antibody preparation of claim 1, wherein said anti-enzyme-nucleic acid covalent complex antibody is produced using a polypeptide antigen having the amino acid sequence set forth in SEQ ID NO:1 or 4.

6. A method for assessing a sample for enzyme-nucleic acid covalent complexes, wherein said method comprises performing an immune-based assay using an anti-enzyme-nucleic acid covalent complex antibody to detect the presence, absence, or amount of said enzyme-nucleic acid covalent complexes within said sample, wherein said anti-enzyme-nucleic acid covalent complex antibody binds to said enzyme-nucleic acid covalent complex and does not bind to the free form of said enzyme or the free form of said nucleic acid, wherein said enzyme is selected from the group consisting of topoisomerase I, topoisomerase II, topoisomerase III, tyrosyl deoxynucleotidyl phosphodiesterase, yeast topoisomerases, protozoal topoisomerases, and bacterial topoisomerases.

7. The method of claim 6, wherein said enzyme is topoisomerase I.

8. The method of claim 6, wherein said enzyme is topoisomerase II.

9. The method of claim 6, wherein said nucleic acid is DNA.

10. The method of claim 6, wherein said anti-enzyme-nucleic acid covalent complex antibody is produced using a polypeptide antigen having the amino acid sequence set forth in SEQ ID NO:1 or 4.

11. The method of claim 6, wherein said immune-based assay comprises immunoblotting, immunofluorescence, or flow cytometry.

12. The method of claim 6, wherein said sample is a tissue biopsy sample.

* * * * *

SEQUENCE LISTING

```
<160> NUMBER OF SEQ ID NOS: 16

<210> SEQ ID NO 1
<211> LENGTH: 16
<212> TYPE: PRT
<213> ORGANISM: Artificial Sequence
<220> FEATURE:
<223> OTHER INFORMATION: synthetically generated polypeptide
<220> FEATURE:
<221> NAME/KEY: MOD_RES
<222> LOCATION: 9
<223> OTHER INFORMATION: PHOSPHORYLATION

<400> SEQUENCE: 1

Cys Leu Gly Thr Ser Lys Leu Asn Tyr Leu Asp Pro Arg Ile Thr Val
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: synthetically generated polypeptide with
      N-terminal cysteine

<400> SEQUENCE: 2

Cys Leu Gly Thr Ser Lys Leu Asn Tyr Leu Asp Pro Arg Ile Thr Val
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: synthetically generated polypeptide
<220> FEATURE:
<221> NAME/KEY: MOD_RES
<222> LOCATION: 9
<223> OTHER INFORMATION: PHOSPHORYLATION
<220> FEATURE:
<221> NAME/KEY: VARIANT
<222> LOCATION: 2, 3, 4, 5, 6, 7, 8, 10, 11, 12, 13, 14, 15, 16
<223> OTHER INFORMATION: Xaa = any amino acid

<400> SEQUENCE: 3

Cys Xaa Xaa Xaa Xaa Xaa Xaa Xaa Tyr Xaa Xaa Xaa Xaa Xaa Xaa Xaa
1               5                   10                  15

<210> SEQ ID NO 4
<211> LENGTH: 16
<212> TYPE: PRT
<213> ORGANISM: Artificial Sequence
```

```
<220> FEATURE:
<223> OTHER INFORMATION: synthetically generated polypeptide
<220> FEATURE:
<221> NAME/KEY: MOD_RES
<222> LOCATION: 9
<223> OTHER INFORMATION: PHOSPHORYLATION

<400> SEQUENCE: 4

Cys Lys Asp Ser Ala Ser Pro Arg Tyr Ile Phe Thr Met Leu Ser Ser
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: synthetically generated polypeptide
<220> FEATURE:
<221> NAME/KEY: MOD_RES
<222> LOCATION: 9
<223> OTHER INFORMATION: PHOSPHORYLATION

<400> SEQUENCE: 5

Cys Lys Asp Ala Ala Ser Pro Arg Tyr Ile Phe Thr Met Leu Ser Thr
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: synthetically generated polypeptide with
      N-terminal cysteine

<400> SEQUENCE: 6

Cys Lys Asp Ser Ala Ser Pro Arg Tyr Ile Phe Thr Met Leu Ser Ser
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: synthetically generated polypeptide with
      N-terminal cysteine

<400> SEQUENCE: 7

Cys Lys Asp Ala Ala Ser Pro Arg Tyr Ile Phe Thr Met Leu Ser Thr
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: synthetically generated polypeptide
<220> FEATURE:
<221> NAME/KEY: MOD_RES
<222> LOCATION: 9
<223> OTHER INFORMATION: PHOSPHORYLATION

<400> SEQUENCE: 8

Cys Asp Ile Ala Phe Gly Thr His His Thr Lys Met Met Leu Leu Leu
1               5                   10                  15

<210> SEQ ID NO 9
<211> LENGTH: 16
<212> TYPE: PRT
<213> ORGANISM: Artificial Sequence
```

```
<220> FEATURE:
<223> OTHER INFORMATION: synthetically generated polypeptide with
      N-terminal cysteine

<400> SEQUENCE: 9

Cys Asp Ile Ala Phe Gly Thr His His Thr Lys Met Met Leu Leu Leu
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: partial polypeptide sequence containing
      phosphorylated amino acid at position 8

<400> SEQUENCE: 10

Leu Gly Thr Ser Lys Leu Asn Tyr Leu Asp Pro Arg Ile Thr Val
1               5                   10                  15

<210> SEQ ID NO 11
<211> LENGTH: 15
<212> TYPE: PRT
<213> ORGANISM: Homo sapiens

<400> SEQUENCE: 11

Leu Gly Thr Ser Lys Leu Asn Tyr Leu Asp Pro Arg Ile Thr Val
1               5                   10                  15

<210> SEQ ID NO 12
<211> LENGTH: 15
<212> TYPE: PRT
<213> ORGANISM: Mus musculus

<400> SEQUENCE: 12

Leu Gly Thr Ser Lys Leu Asn Tyr Leu Asp Pro Arg Ile Thr Val
1               5                   10                  15

<210> SEQ ID NO 13
<211> LENGTH: 15
<212> TYPE: PRT
<213> ORGANISM: Gallus gallus

<400> SEQUENCE: 13

Leu Ser Thr Ser Lys Leu Asn Tyr Leu Asp Pro Arg Ile Ser Val
1               5                   10                  15

<210> SEQ ID NO 14
<211> LENGTH: 15
<212> TYPE: PRT
<213> ORGANISM: Drosophila melanogaster

<400> SEQUENCE: 14

Leu Gly Thr Ser Lys Leu Asn Tyr Leu Asp Pro Arg Ile Ser Val
1               5                   10                  15

<210> SEQ ID NO 15
<211> LENGTH: 15
<212> TYPE: PRT
<213> ORGANISM: C. elegans

<400> SEQUENCE: 15

Leu Gly Thr Ser Lys Leu Asn Tyr Ile Asp Pro Arg Ile Thr Val
1               5                   10                  15
```

```
<210> SEQ ID NO 16
<211> LENGTH: 15
<212> TYPE: PRT
<213> ORGANISM: Saccaromyces cerevisiae

<400> SEQUENCE: 16

Leu Gly Thr Ser Lys Ile Asn Tyr Ile Asp Pro Arg Leu Ser Val
1               5                   10                  15
```